United States Patent
Moore et al.

(10) Patent No.: US 6,231,515 B1
(45) Date of Patent: May 15, 2001

(54) SAFETY MECHANISM AND METHOD TO PREVENT ROTATING IMAGING GUIDE DEVICE FROM EXITING A CATHETER

(75) Inventors: Thomas C. Moore, Fremont; Larry D. Wasicek, San Jose; Ronald J. Jabba, Redwood City, all of CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/229,277

(22) Filed: Jan. 13, 1999

(51) Int. Cl.[7] .................................................. A61B 8/00
(52) U.S. Cl. ............................................................ 600/466
(58) Field of Search ..................................... 600/466, 465, 600/459, 468, 469

(56) References Cited

U.S. PATENT DOCUMENTS

| | | | |
|---|---|---|---|
| 5,054,492 | * 10/1991 | Scribner et al. | 600/466 |
| 5,131,397 | * 7/1992 | Crowley | 600/466 |
| 5,437,282 | * 8/1995 | Koger et al. | 600/466 |
| 5,485,845 | 1/1996 | Verdonk et al. | 128/662.06 |
| 5,671,748 | * 9/1997 | Itoi | 600/459 |

FOREIGN PATENT DOCUMENTS

| | | |
|---|---|---|
| WO 91/02489 | 3/1991 | (WO) . |
| WO 96/39081 | 12/1996 | (WO) . |

* cited by examiner

*Primary Examiner*—Marvin M. Lateef
*Assistant Examiner*—Maulin Patel
(74) *Attorney, Agent, or Firm*—Townsend and Townsend and Crew LLP

(57) ABSTRACT

The invention provides exemplary systems and methods to prevent rotation of an imaging device if the imaging device is advanced beyond a distal end of a catheter. In one exemplary embodiment, a catheter is provided which comprises a catheter body having a proximal end, a distal end and a lumen which terminates in an exit port at the distal end. The lumen is configured to receive a rotatable imaging device having an ultrasonic imaging element. An ultrasonically recognizable pattern is disposed proximally to or at the exit port. The pattern is adapted to reflect a signal from the imaging element to produce a unique detectable image which in turn is employed to stop rotation of the imaging device.

29 Claims, 6 Drawing Sheets

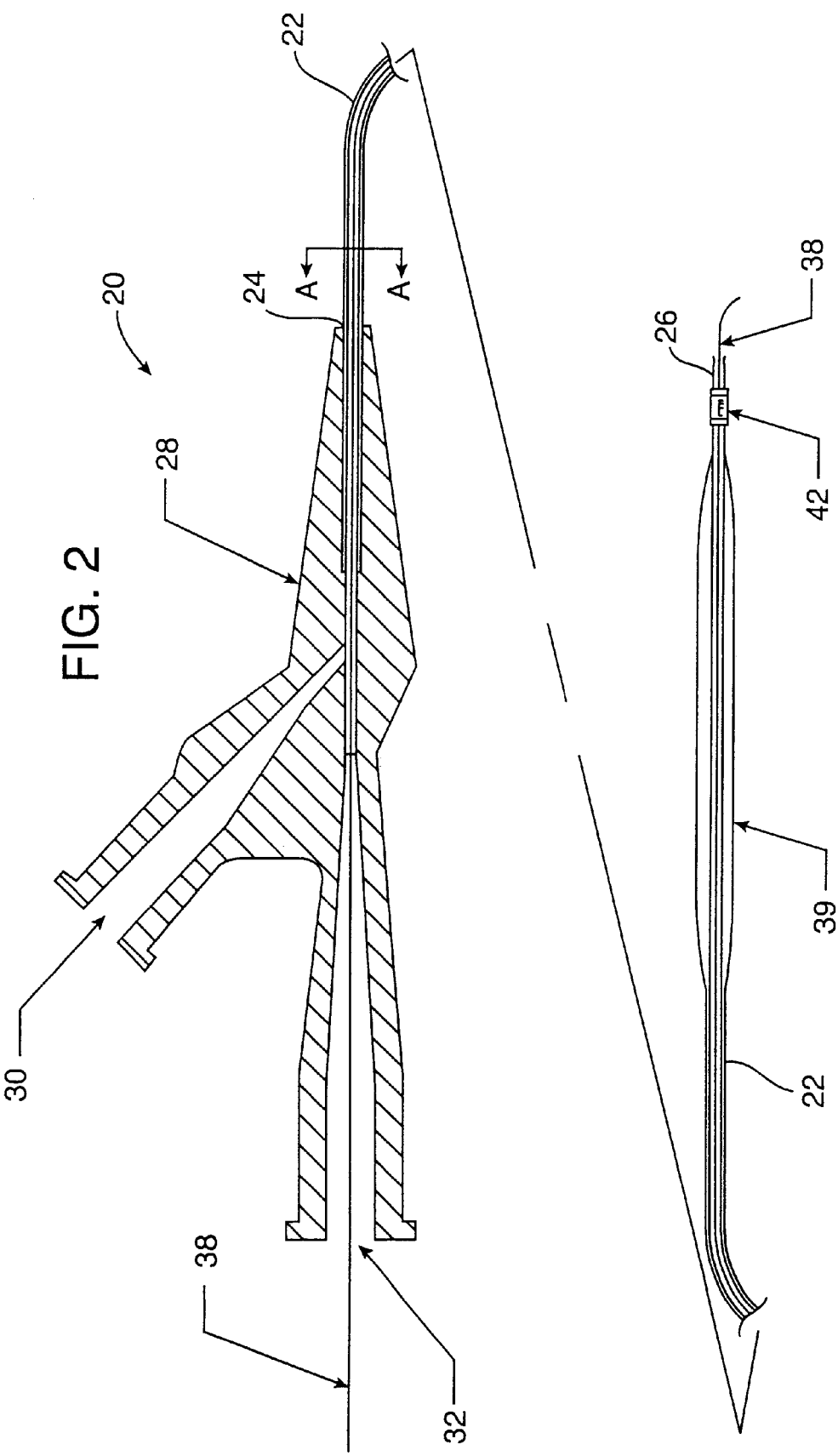

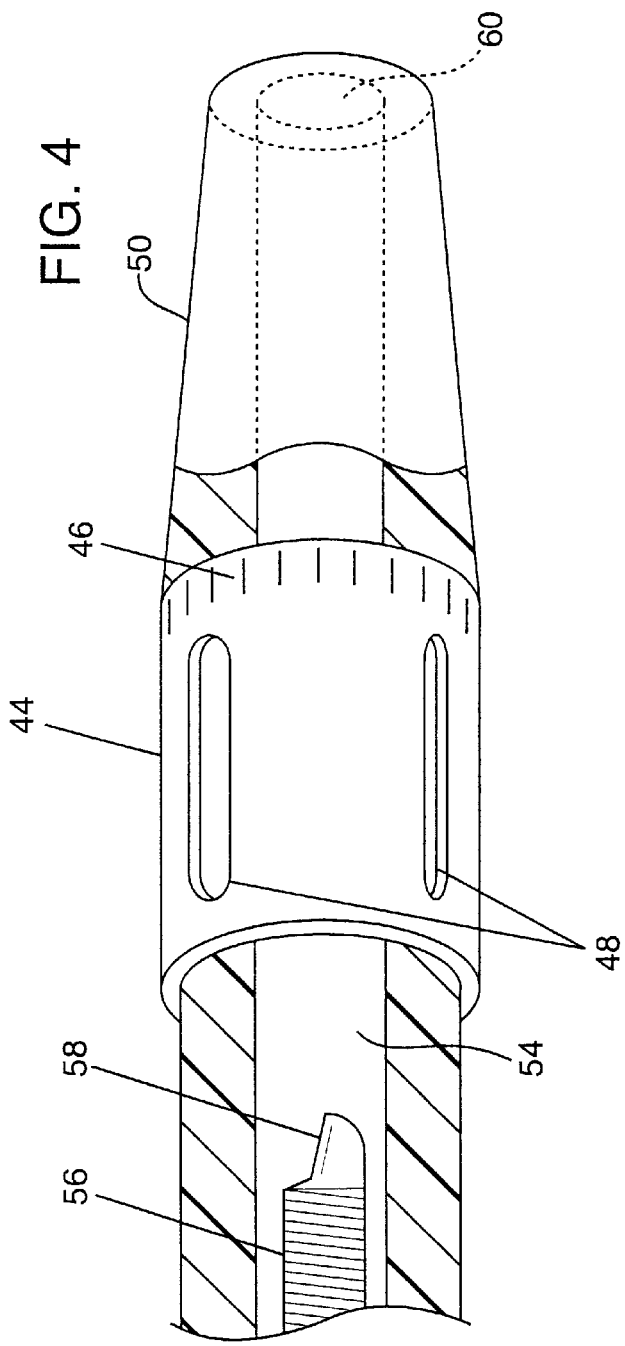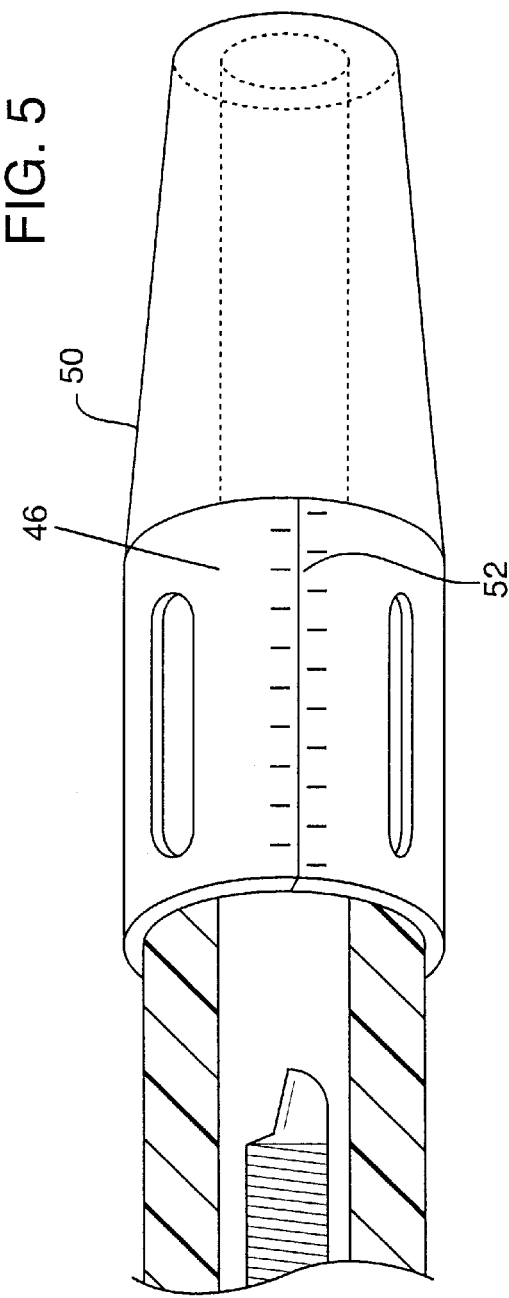

SAFETY MECHANISM AND METHOD TO PREVENT ROTATING IMAGING GUIDE DEVICE FROM EXITING A CATHETER

BACKGROUND OF THE INVENTION

The invention relates generally to the field of ultrasonic imaging, and in particular to the imaging of body lumens or cavities. More specifically, the invention relates to the use of imaging devices that are rotated at high speeds to produce an image of a body lumen or cavity.

The use of rotatable imaging devices to produce an image of a body lumen is well known. For example, one pioneering effort is described in U.S. Pat. No. 4,794,931, the complete disclosure of which is herein incorporated by reference. In U.S. Pat. No. 4,794,931, a drive cable having an imaging element at a distal end is rotated within a catheter to produce an image of a diseased region prior to therapy.

Recently, there has been an advancement in the field of rotatable imaging devices where the size of the imaging devices has been substantially reduced. For instance, one such imaging device is described generally in copending U.S. application Ser. No. 09/017,578, filed Feb. 3, 1998, the complete disclosure of which is herein incorporated by reference. Such an imaging device is small enough to operate within traditional guide wire lumens of therapeutic catheters, such as angioplasty balloon catheters.

One potential problem that may arise when operating imaging devices within catheter lumens having a distal exit port, such as within guide wire lumens of therapeutic catheters, is that the rotating imaging device may accidentally be advanced beyond the distal exit port and into the body lumen, thereby posing a risk of damage to the luminal wall.

Hence, it would be desirable to provide a way to prevent the unwanted advancement of a rotating imaging device beyond a distal exit port of a catheter. Such a safeguard should be reliable and easy to use to maximize its acceptance in the industry.

SUMMARY OF THE INVENTION

The invention provides exemplary techniques for preventing the unwanted advancement of a rotating imaging device beyond an exit port of a catheter and into a body lumen. In one exemplary embodiment, a catheter is provided which comprises a catheter body having a proximal end, a distal end and a lumen, such as a guide wire lumen, which terminates in an exit port at the distal end. An ultrasonically recognizable pattern is disposed proximally to or at the exit port. The recognizable pattern is provided to produce a unique image when imaged with an imaging element of an imaging device which is rotated within the lumen.

The catheter is preferably included as part of a system which includes a controller having a motor to rotate the imaging device. The controller is configured to stop rotation of the imaging device upon receipt of a signal from the imaging device indicating that the presence of the recognizable pattern has been detected. In this way, once the imaging device has been advanced through the lumen and up to the recognizable pattern, the presence of the pattern will be detected by the controller which will stop rotation of the imaging device. As such, if the imaging device is advanced beyond the exit port, the imaging device will not be rotating, thus substantially reducing the chances of damaging the luminal or cavity wall. Alternatively, if the motor is employed to also translate the imaging device, the signal may be employed to stop translation of the imaging device so that the rotating imaging device will not be advanced distally beyond the exit port.

A wide variety of recognizable patterns may be provided to indicate when the imaging device has advanced too far within the lumen. For example, the pattern may comprise a tubular reflective member which is crimped or otherwise attached about the tubular body. Other patterns which may be employed include ultrasonically reflective materials having a variety of shapes and sizes which may be attached to or integrally formed within the catheter body, echogenic coatings, changes in the diameter of the catheter body, the distal end of the catheter body, and the like. Preferably, the pattern is fashioned to have a shape or configuration which allows it to be differentiated from the rest of the image. For example, the pattern may include a plurality of elongate apertures which will appear as voids in the resulting image, thus differentiating the pattern from a stent. As the controller recognizes the voids, rotation of the imaging device is stopped.

The catheter is preferably a therapeutic catheter having a therapeutic element for treating a region of the body lumen. For example, the therapeutic element may comprise an angioplasty balloon. As another example, the therapeutic element may comprise a stent delivery system. As a further examples, the therapeutic element may comprise a laser or a rotatable cutting element.

In another aspect, the lumen preferably extends the length of the catheter body. In this way, the catheter may be inserted into the body lumen over a guide wire in an over-the-wire manner. Typically, the lumen will have a diameter in the range from about 0.25 mm to about 5 mm, and from about 0.25 mm to about 0.5 mm for applications within the coronary arteries. The imaging device preferably has a diameter in the range from about 0.20 mm to about 2 mm.

The invention further provides an exemplary attachment for a catheter that has a lumen terminating in an exit port at a distal end of the catheter. The attachment comprises a tubular member which may be coupled about the catheter proximal to the exit port. The tubular member is constructed of an ultrasonically reflective material and has unique shape that will produce a unique image when imaged with an ultrasonic imaging element which is rotated within the lumen. In this way, a catheter may be conveniently modified so that it may be used with a safety system that will stop rotation of an imaging element upon detection of the tubular member.

In one exemplary method of the invention, a body lumen is visualized by introducing a catheter into the body lumen. The catheter comprises a catheter body having a lumen which terminates in an exit port and an ultrasonically recognizable pattern disposed at or near the exit port. An imaging device is introduced through the lumen and positioned so that an imaging element is at a location that is to be imaged. The imaging device is rotated while the imaging element is actuated to produce an image of the body lumen. Rotation of the imaging device is stopped if an image of the pattern is detected so that advancement of the rotating imaging device beyond the exit port is prevented. Alternatively, translation of the imaging device may be stopped so that the rotating imaging device will not moved distally beyond the exit port.

In one aspect, the catheter is introduced into the body lumen by advancing the catheter over a guide wire. Once properly positioned, the guide wire is withdrawn and the imaging device is introduced into the guide wire lumen.

In another aspect, a therapeutic element is deployed while the imaging device is rotating to produce an image of the therapeutic element. In this way, the body lumen may be visualized throughout the therapeutic procedure. For example, visualization may occur while a balloon is being inflated or a stent is being deployed. The pattern preferably has a unique shape to allow it to be easily differentiated from the therapeutic element. In this way, once the unique shape is detected, rotation of the imaging device may be stopped.

BRIEF DESCRIPTION OF THE DRAWINGS

FIG. 2 is a cross-sectional side view of a catheter having a tubular reflective member disposed near a distal end according to the invention.

FIG. 4 is a partially cut-away side view of a distal end of a catheter having the tubular reflective member of FIG. 3.

FIG. 5 illustrates an alternative embodiment of a tubular reflective member disposed about a distal end of a catheter according to the invention.

DETAILED DESCRIPTION OF THE SPECIFIC EMBODIMENTS

Figure 1:
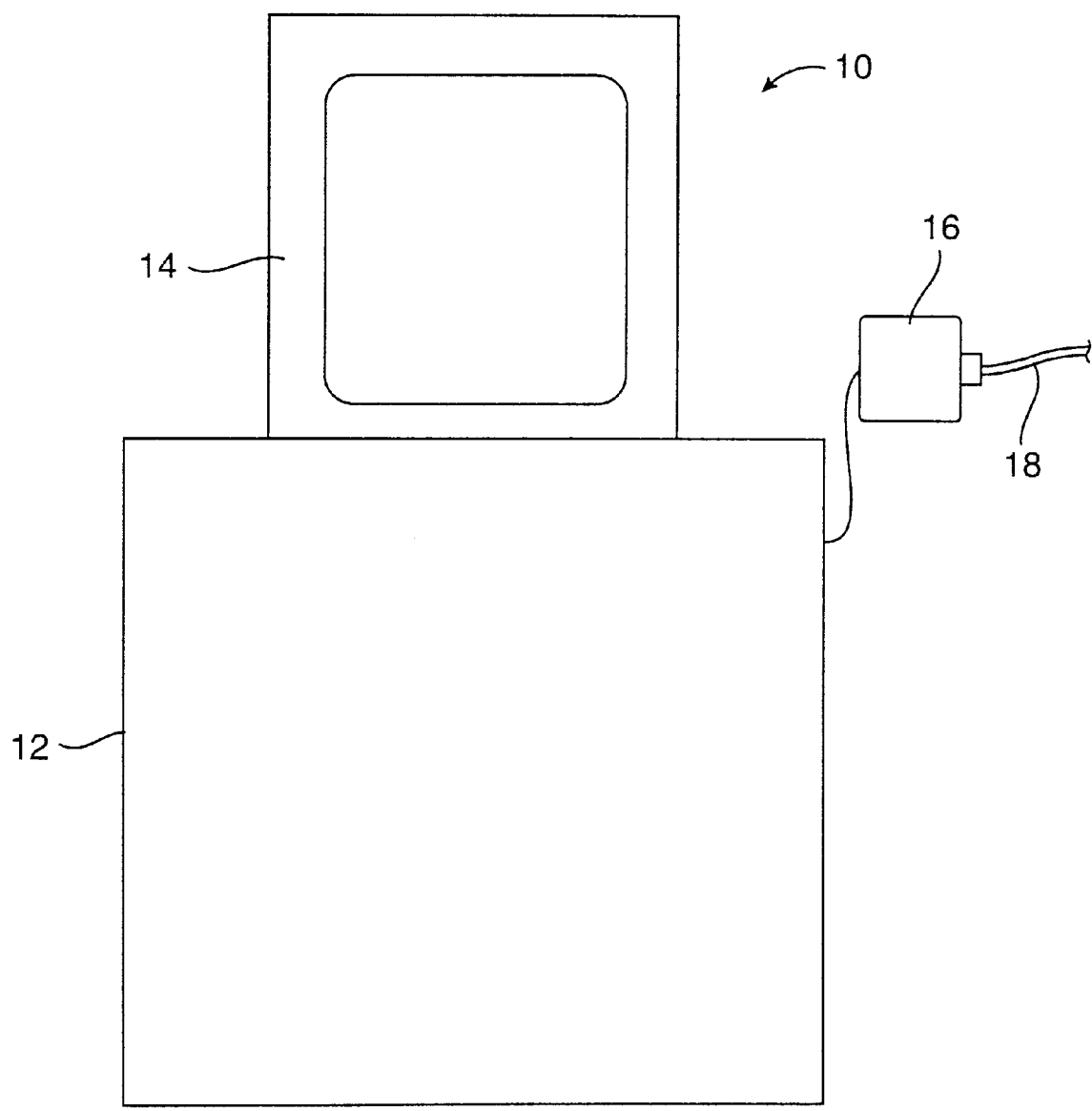
FIG. 1 is a schematic view of an exemplary imaging system according to the invention.

The invention provides various systems and techniques to prevent the advancement of a rotating imaging device beyond a distal exit port of a catheter. In this way, if the imaging device is inadvertently advanced beyond the exit port and into a body lumen or cavity, the techniques provided by the invention will stop rotation of the imaging device to substantially reduce or eliminate the risk of perforating the wall of the body lumen.

The invention may be used with essentially any rotatable imaging device which is rotated within a lumen or cavity of a catheter body to produce an image. Such imaging devices typically comprise an elongate drive cable having an ultrasonic imaging element or transducer disposed at a distal end. Such imaging devices include, among others, imaging cores, imaging wires, imaging guide wires, and the like. Merely by way of example, rotatable imaging devices which may be used with the invention are described in U.S. Pat. No. 4,794,931, previously incorporated by reference, and in copending U.S. application Ser. No. 09/017,578, filed Feb. 3, 1998 and Ser. No. 60/059,718, filed Sep. 22, 1997, the disclosures of which are herein incorporated by reference.

The rotatable imaging devices of the invention may have a wide range of outer dimensions, including outer diameters in the range from about 0.20 mm to about to about 0.5 mm for applications within the coronary arteries. Such a range of diameters allows the imaging devices to be used within conventional guide wire lumens.

Catheters which may be used with the invention preferably comprise a catheter body having a proximal end, a distal end and at least one lumen which terminates at an exit port at the distal end. In many cases, the lumen will comprise a guide wire lumen which is employed to introduce the catheter into a body lumen in an over-the-wire manner. Following insertion, the guide wire lumen serves as an imaging lumen to receive the imaging device so that an image may be produced. Because the lumen terminates at the distal end, the invention provides techniques for stopping rotation of the imaging device either before or upon the exit of the imaging device from the exit port. Exemplary catheters having a lumen which terminates in an exit port at the distal end include PTCA catheters, PCA catheters, various other balloon catheters, atherectomy catheters, "common lumen" catheters as described generally in U.S. Pat. No. 5,314,408, the complete disclosure of which is herein incorporated by reference, and the like. The imaging lumens of such catheters have a diameter which is large enough to receive the rotatable imaging device so that an image may be produced.

The invention may be used in connection with a variety of diagnostic and therapeutic procedures which involve the use of a rotatable imaging device. Such procedures can include, for example, imaging in real time stent deployment and placement, imaging during placement of radiation devices in radiation procedures, imaging during directional coronary atherectomy procedures (DCA), imaging during placement of a balloon during balloon angioplasty procedures, imaging while placing stent grafts, imaging during neurology procedures, imaging during urology procedures, imaging during gastrointestinal procedures, imaging intracardiac structures during ablation, and the like.

Advancement of the rotating imaging device beyond the distal exit port is preferably accomplished by providing an ultrasonically recognizable pattern at or proximal to the distal end of the catheter body. During imaging, the imaging element captures a reflected signal which is sent to a controller to produce an image. When the imaging element reaches the pattern, a signal is reflected indicating the presence of the pattern. Once the pattern is detected by the controller, rotation of the imaging device is stopped so that the imaging device will not be rotating when advanced beyond the distal end of the catheter body. In one alternative, a motor which is employed to translate the imaging device through the catheter body may be stopped when the pattern is detected. In this way, the imaging device will be prevented from distally advancing beyond the exit port.

A wide variety of ultrasonically reflective pattern may be employed to assist in stopping rotation of the imagine device upon detection of the pattern. For example, the pattern may comprise a tubular reflective element that is disposed about the catheter body. In this way, an existing catheter may easily be modified to include an ultrasonically reflective pattern that may be detected to stop rotation of the imaging device.

Other ultrasonically reflective patterns include echogenic coatings, such as Echo-Coat™, that provide an acoustically reflective interface between the catheter and the coating. Such coatings may be blended in the catheter body or applied to an external surface of the catheter body. Preferably, the remainder of the catheter body is construct of an echo translucent or an acoustically transparent polymer(s) so that the remainder of the catheter body is not displayed in the image produced on the monitor. Such coatings may be applied circumferentially or in any type of pattern that may be recognized and detected.

Other possible ultrasonically recognizable patterns include the use of ultrasonically reflective polymers which are disposed at or near the distal end of the catheter body. Such polymers may be formed as part of a co-extrusion or as a blended material within the catheter body. Such polymers are preferably fashioned in a unique shape or composition to facilitate discernment of the pattern. As another alternative, radiopaque markers may be disposed on or within the catheter body and may be constructed from materials such as gold, tantalum, platinum, palladium, and the like. Such markers may be placed at known distances from each other. The controller may be configured to detect these distances in the resulting image to stop rotation of the imaging device. Still further alternatives include the use of holes disposed in the catheter body or a change in the diameter of the imaging lumen of the catheter. As still another alternative, the distal end of the catheter body may be detected to stop rotation of the imaging device. In summary, the ultrasonically reflective pattern may comprise any detectable pattern that may be differentiated from the rest of the image produced to allow system software to stop the imaging element from rotating and/or translating.

In one alternative embodiment, spring-loaded contacts may be provided at the distal end of the catheter. In this way, when the imaging device passes through the distal end, the contacts are opened causing a break in an electrical circuit.

Referring now to FIG. 1, an exemplary embodiment of an ultrasonic imaging system 10 will be described. System 10 comprises a controller 12 which is coupled to a monitor 14. Controller 12 is also coupled to a motor 16 which is employed to rotate a drive cable 18 of an imaging device. Controller 12 includes circuitry and software which is configured to receive a reflected signal from an ultrasonic imaging element and to produce an image based on the reflective signal on monitor 14. An exemplary controller which may be used with the invention is a Clear View Ultra™ intraluminal ultrasound system, commercially available from Boston Scientific Corporation. A variety of commercially available motors may be employed to rotate drive cable 18.

Figure 2A:
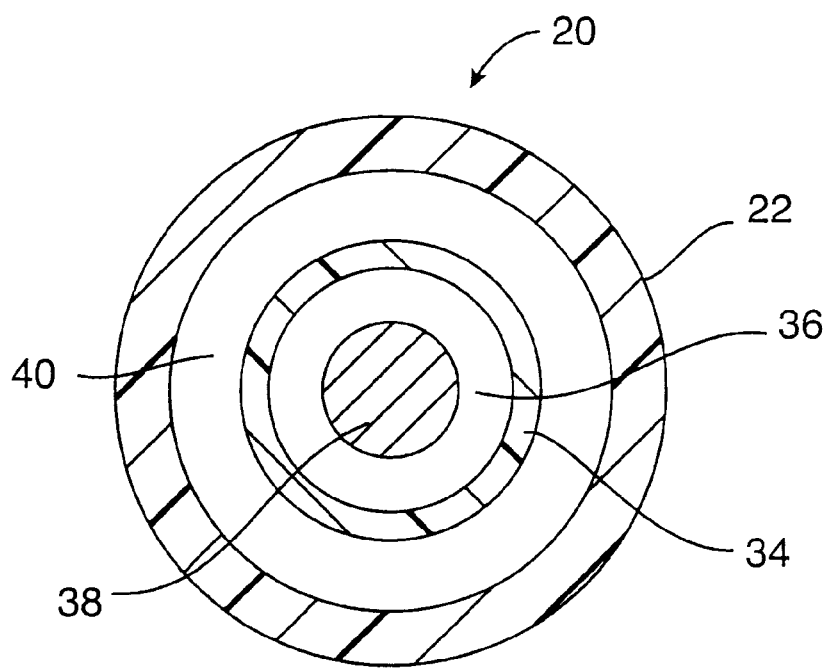
FIG. 2A is a cross-sectional view of the catheter of FIG. 2 taken along lines A—A.

Referring now to FIG. 2, one type of catheter 20 which may be utilized with system 10 will be described, it being appreciated that a wide variety of catheters may be employed with the invention as previously described. Catheter 20 is representative of a conventional PTCA catheter which comprises a catheter body 22 having a proximal end 24 and a distal end 26. Coupled to proximal end 24 is a hub 28 having a balloon inflation port 30 and a guide wire or imaging device entry port 32. As best shown in FIG. 2A, disposed within catheter body 22 is a sheath 34 having a central lumen 36. Disposed within lumen 36 is a guide wire 38. As illustrated in FIG. 2, guide wire 38 extends between entry port 32 and distal end 26. As is known in the art, catheter 20 may be inserted through a body lumen by first inserting guide wire 38 into the lumen and then advancing catheter 20 over guide wire 38 in an over-the-wire manner.

Catheter 20 further includes a balloon 39 which is inflated by introducing a fluid through balloon inflation port 30. As best illustrated in FIG. 2A, a balloon inflation lumen 40 is provided between catheter body 22 and sheath 34 to deliver the fluid from port 30 to balloon 39.

Also disposed at distal end 26 is a tubular reflective member 42. Reflective member 42 is constructed of an ultrasonically reflective material, such as stainless steel, and is placed about catheter body 22. In this way, when guide wire 38 is withdrawn from lumen 36 and an imaging device is inserted through lumen 36 and rotated to produce image, reflective member 42 will be visualized by the imaging device if advanced up to reflective member 42. The placement of reflective member 42 just distal to balloon 39 is advantageous since the imaging element will often be employed to visualize proper placement of balloon 39. In the event that the imaging element is advanced beyond balloon 39, the presence of reflective member 42 will be detected so that rotation and/or translation of the imaging device may be stopped.

Figure 3:
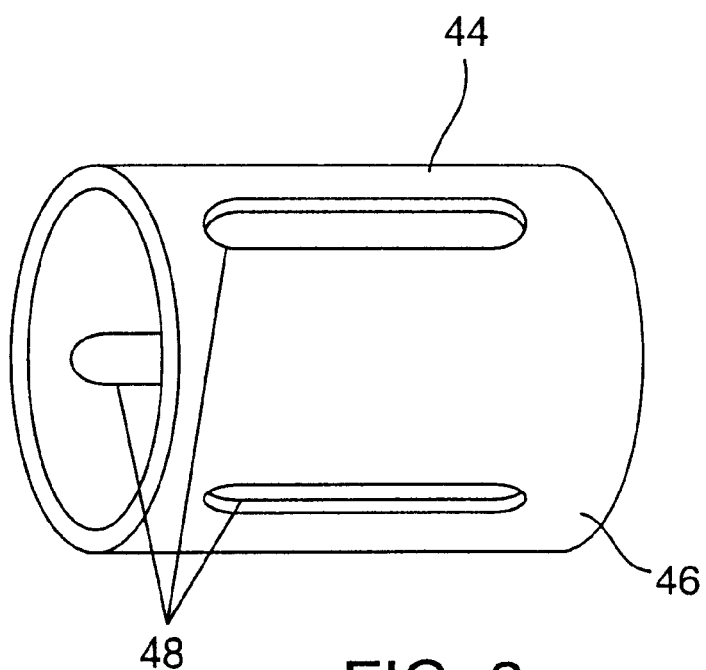
FIG. 3 is a perspective view of an exemplary tubular reflective member according the invention.

Referring now to FIG. 3, an exemplary embodiment of a tubular reflective member 44 will be described. Reflective member 44 comprises a tubular body 46 that is constructed of an ultrasonically reflective or opaque material, such as stainless steel. Tubular body 46 includes three elongate apertures 48. The placement of apertures 48 is advantageous in that the resulting image produced by the imaging device is essentially the inverse image of that produced by a stent as described in greater detail hereinafter. In this way, reflective member 44 may easily be distinguished from a stent. Although shown with three elongate apertures, it will be appreciated that the number, size and geometry of the apertures may be varied. Use of a tubular body is particularly advantageous in that it may easily be crimped or otherwise attached about an existing catheter to provide the catheter with an ultrasonically reflective pattern that may be detected to stop rotation of the imaging device. As one example, tubular body 46 may be crimped at one end to secure tubular body 46 to a catheter body 50 as illustrated in FIG. 4. Alternatively, as illustrated in FIG. 5, tubular body 46 may include a longitudinal slit 52 to facilitate the crimping of tubular body 46 about catheter body 50.

Figure 6:
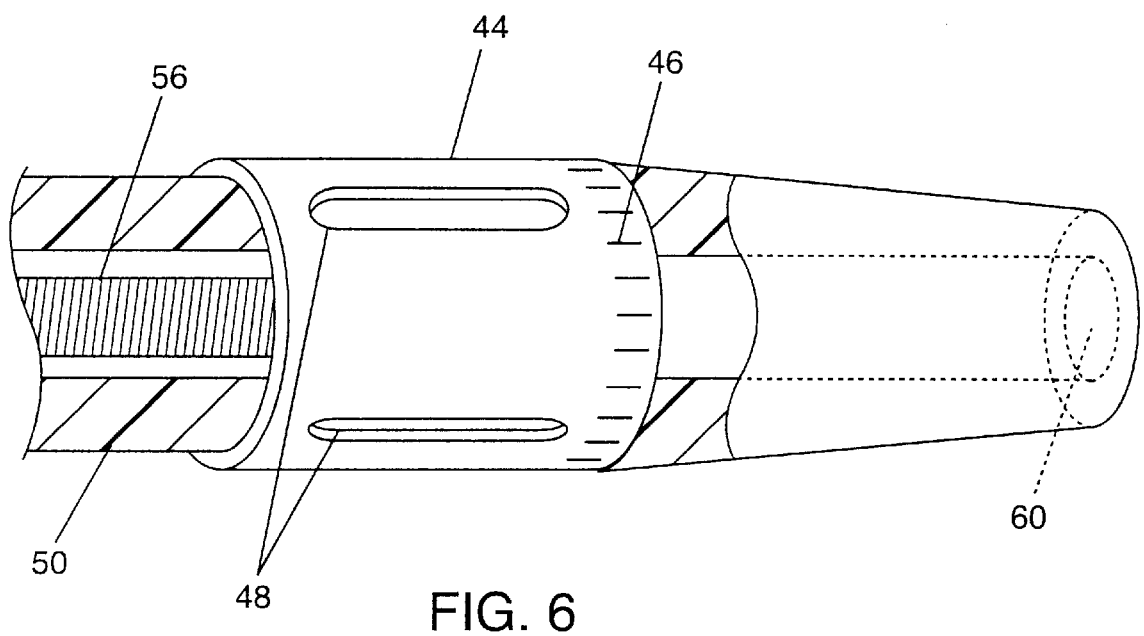
FIG. 6 illustrates the catheter of FIG. 4 having an imaging element of a rotating imaging device disposed within the tubular reflective member according to the invention.
Figure 7:
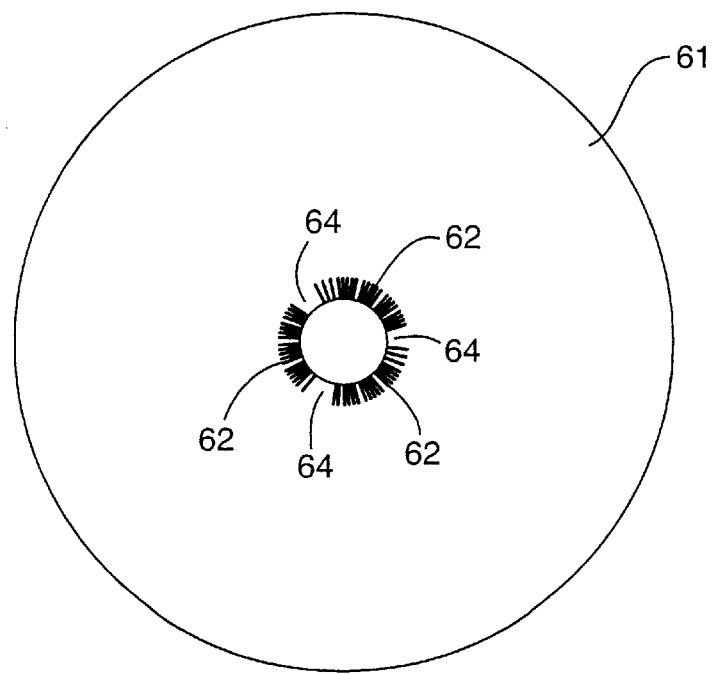
FIG. 7 illustrates a reflected image that is detected by the imaging element of FIG. 6 when disposed within the tubular reflective member according to the invention.

As illustrated in both FIGS. 4 and 5, catheter body 50 includes a lumen 54 into which a rotatable imaging device 56 is received. Imaging device 56 includes an imaging element 58 which is rotated within lumen 54 to produce an image of the area surrounding catheter body 50 as is known in the art. Catheter body 50 further includes an exit port 60. To prevent the advancement of imaging device 56 through exit port 60 while imaging device 56 is rotating, tubular reflective member 44 is placed just proximal to or at exit port 60. As illustrated in FIG. 6, when imaging device 56 is distally advanced within lumen 54, imaging element 58 will eventually reach reflective member 44. The resulting image that is detected by reflective member 44 is produced on a monitor screen as illustrated in FIG. 7. In image 61, three echos 62 are illustrated and represent the metallic areas of reflective member 44. Three voids 64 exist which are representative of apertures 48 in tubular body 46. When the controller detects the pattern of voids 64, it knows that imaging device 56 has been advanced up to tubular reflective member 44. As such, the controller will send a signal to stop rotation of imaging device 56 so that if it is advanced beyond exit port 60 it will not be rotating, thereby posing no risk of danger to the luminal wall of the patient.

Referring back now to FIG. 1, a description of one exemplary algorithm employed by controller 12 to stop rotation of motor 16 when the presence of an ultrasonically reflective pattern is detected will be described. Such an algorithm is particularly useful when employing a tubular member with three equidistantly spaced slots which are parallel to the axis of the tubular member as illustrated in FIG. 3. Such slots provide a distinct ultrasonically detectable signature that does not occur naturally within human vessel, or as a byproduct of transcatheter or surgical interventions.

In this embodiment, controller 12 preferably acquires data in Polar (R-θ) format. The data acquired includes a series of individual frames (one complete 360 degree rotation of the imaging device) of sample points. Controller 12 preferably acquires 256 equally spaced 8-bit samples along a vector, with 256 vectors per frame (a frame being one complete 360 degree rotation of the imaging device). One frame, or data set, is therefore a 256 by 256 array of 8-bit sample values. The distance from the transducer face (R), of a given data point, is determined by multiplying the sample spacing (propagation speed of ultrasound times the sample period) by the sample number (depth) along a given vector. The angle (θ) in degrees relative to the beginning of the frame is determined by dividing 360 degrees by the number of vectors within a frame times the vector number (360 degrees/256*vector number). Hence, the 8-bit sample at array position [0,0] is acquired at the face of the transducer, when the imaging device is directed at the 12 O'clock position [255,127] is the last sample on the vector pointed at the 6 O'clock position (middle of the frame 180 degrees).

The face of the transducer on the imaging device is located a fixed depth within the catheter body. At the beginning of a vector, acoustic energy is transmitted from the transducer. The receiver begins sampling the vector, and an acoustic near field artifact is generated that typically settles to a sample value less than 50 (⅕ full-scale) by the outer edge of the catheter body. When the imaging device is advanced into the tubular member, the reflective material of which the tubular member is constructed generates a return echo at the catheter body that will have a sample value of at least 200 (⅘ full-scale). This high value is present on all vectors directed at the tubular member. When the imaging device is pointed at the slot within the tubular member, the sample values will return to less than 50, and remain at this low value until the tubular member is again encountered. A frame of data sampled from within the tubular member contains a pattern of three long (approximately 64 vectors) highs, and three short (approximately 21 vectors) lows (depending on the thickness of the slots) at the outer edge of the catheter body. This pattern is present when the sample values are wrapped around so that the beginning and end of the frame do not form separate highs and lows. A digital signal processor or other suitable device is employed to continuously monitor the sample values searching for this pattern. When such a pattern is encountered, and repeated over a fixed number of frames, then the digital signal processor commands the motor rotating the imaging device to stop.

Figure 8:
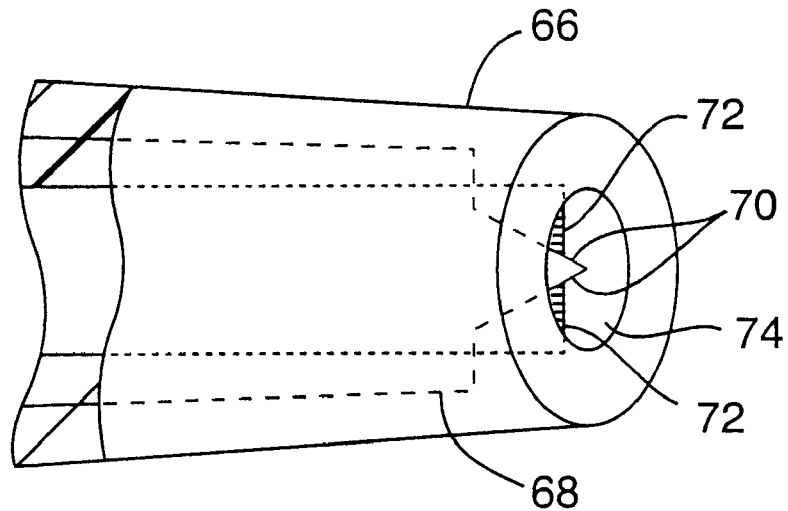
FIG. 8 is a schematic view of a distal end of a catheter showing an electrical circuit which is opened when an imaging device is advanced beyond a distal end of the catheter according to the invention.

Referring now to FIG. 8, an alternative embodiment of a catheter body 66 will be described. For convenience of discussion, only a distal end of catheter body 66 will be described. Disposed in catheter body 66 is an electrical circuit 68 having a pair of contacts 70 which are biased together by a pair of springs 72. When contacts 70 are adjacent to each other, the circuit is closed. If, however, an imaging device is passed through an exit port 74, contacts 70 will move apart from each other and cause the circuit to open, providing that the imaging device tip is non-conductive. The opening of circuit 68 may then be detected by the controller to stop rotation of the imaging device in a manner similar to that described with previous embodiments.

Figure 9:
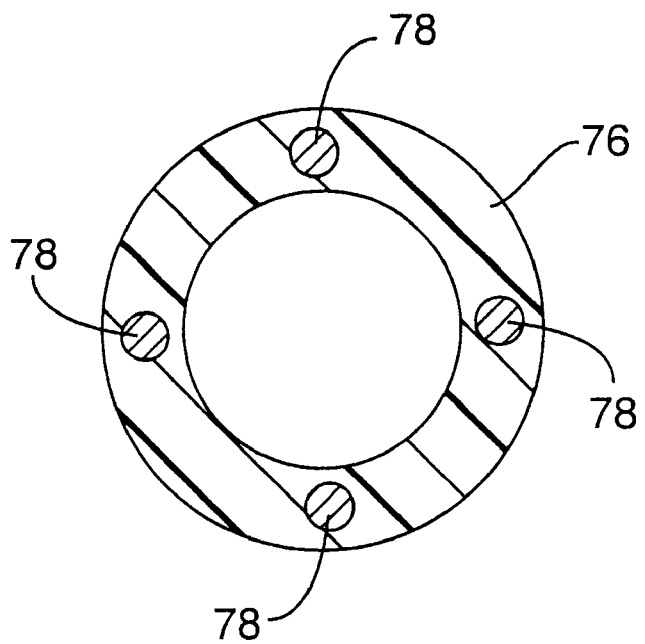
FIG. 9 illustrates a cross-sectional end view of a distal end of a catheter having a plurality of radiopaque markers disposed within the catheter body according to the invention.

Referring to FIG. 9, another alternative embodiment of a catheter body 76 will be described. Catheter body 76 is shown in cross-section and includes four equally spaced radiopaque markers 78. Markers 78 are disposed at a distal end of catheter body 76 and are spaced at known angles relative to each other so that the image produced by the imaging device may be detected by the controller to stop rotation of the imaging device. Although markers 78 are shown within catheter body 76, it will be appreciated that markers 78 may be disposed externally on catheter body 76. Further, the shape, size, geometry and configuration of markers 78 may be varied to produce a distinct recognizable image that may be employed to stop rotation of the imaging device.

In another alternative of the invention, two or more ultrasonically distinct patterns may be positioned such that a region of interest is defined. For example, such patterns may be placed at two ends of a balloon or stent. These patterns may be employed to produce a start pattern and a stop pattern that is recognized by the controller. In this way, the imaging device may automatically be moved back and forth within the region of interest to provide multiple views of the region of interest.

Although the foregoing invention has been described in detail for purposes of clarity of understanding, it will be appreciated that certain modifications may be practiced within the scope of the appended claims.

What is claimed is:

1. A catheter comprising:
   a catheter body having a proximal end, a distal end where the catheter body distally terminates and a lumen which extends to and terminates at the distal end to define an exit port in the distal end, wherein the lumen is adapted to receive a rotatable imaging device having an ultrasonic imaging element; and
   an ultrasonically recognizable pattern disposed proximally to or at the exit port, the pattern being adapted to reflect a signal from the imaging element to produce a unique detectable image that may be used to stop rotation of the imaging device before it exits the exit port.

2. A catheter as in claim 1, wherein the recognizable pattern comprises a tubular reflective member which is affixed about the catheter body, and wherein the lumen comprises a guide wire lumen.

3. A catheter as in claim 2, wherein the tubular reflective member includes a plurality of elongate apertures.

4. A catheter as in claim 1, further comprising a therapeutic element coupled to the catheter body.

5. A catheter as in claim 4, wherein the therapeutic element is selected from the group of elements consisting of balloons, stents, stent grafts, lasers, and rotatable cutters.

6. A catheter as in claim 1, wherein the lumen extends the length of the catheter body.

7. A catheter as in claim 1, wherein the lumen a diameter in the range from about 0.20 mm to about 5 mm.

8. A catheter as in claim 1, wherein the recognizable pattern is constructed of a material selected from the group consisting of stainless steel, echogenic coatings, polymers, filled polymers, gold, tantalum, platinum, and palladium.

9. A catheter system comprising:
   a catheter comprising a catheter body having a proximal end, a distal end, a lumen which terminates in an exit port at the distal end, and an ultrasonically recognizable pattern disposed proximally to or at the exit port;
   an elongate imaging device having a proximal end, a distal end, and an imaging element near the distal end, the imaging device being receivable in the lumen; and a controller having a motor which is adapted to rotate the imaging device, wherein the controller is adapted to stop rotation of the imaging device upon receipt of a signal from the imaging device indicating that the presence of the recognizable pattern has been detected.

10. A catheter system as in 9, wherein the recognizable pattern comprises a tubular reflective member which is crimped about the catheter body, and wherein the lumen comprises a guide wire lumen.

11. A catheter as in claim 10, wherein the tubular member includes a plurality of elongate apertures.

12. A catheter as in claim 9, further comprising a therapeutic element coupled to the catheter body.

13. A catheter as in claim 12, wherein the therapeutic element is selected from the group of elements consisting of balloons, stents, stent grafts, lasers, and rotatable cutters.

14. A catheter as in claim 9, wherein the lumen extends the length of the catheter body.

15. A catheter as in claim 9, wherein the lumen has a diameter in the range from about 0.20 mm to about 5 mm.

16. A catheter as in claim 9, wherein the reflective element is constructed of a material selected from the group consisting of stainless steel, echogenic coatings, polymers, filled polymers, gold, tantalum, platinum, and palladium.

17. A catheter system as in claim 9, wherein the imaging device has a diameter in the range from about 0.20 mm to about 2 mm.

18. An attachment for a catheter, the attachment comprising:

a tubular member which is adapted to be attached over the entire catheter proximal to an exit port of the catheter, the tubular member being constructed of an ultrasonically reflective material and having a unique shape which is adapted to produce a unique image when visualized with an ultrasonic image element which is rotated in a lumen of the catheter.

19. A method for visualizing a body lumen, the method comprising:

introducing a catheter into a body lumen, the catheter comprising a catheter body having a proximal end, a distal end, a lumen which terminates in an exit port at the distal end, and an ultrasonically recognizable pattern disposed proximally to or at the exit port;

introducing an elongate imaging device into the lumen, the imaging device having an imaging element near a distal end;

rotating the imaging device and actuating the imaging element to produce an image of the body lumen; and stopping rotation of the imaging device when an image of the recognizable pattern is detected to prevent advancement of the rotating imaging device through the exit port and into the body lumen.

20. A method as in claim 19, further comprising inserting the catheter over a guide wire to introduce the catheter into the body lumen, and withdrawing the guide wire from the lumen prior to introducing the imaging device.

21. A method as in claim 19, further comprising deploying a therapeutic element from the catheter while producing the image of the body lumen.

22. A method as in claim 21, wherein the therapeutic element is a balloon which is inflated within the body lumen.

23. A method as in claim 21, wherein the therapeutic element is a stent which is expanded within the body lumen.

24. A method as in claim 19, wherein the recognizable pattern comprises a reflective element having a unique shape, and wherein rotation of the imaging device is stopped when a signal from the ultrasonic imaging element indicates detection of the unique shape.

25. A method as in claim 24, wherein the reflective element includes at least one elongate aperture which produces a void in an image generated by the imaging device.

26. A method for preventing the advancement of a rotating imaging device beyond an exit port of a catheter, the method comprising:

rotating an imaging device having an imaging element within a lumen of a catheter, the imaging device having an ultrasonically recognizable pattern near or at a distal end;

moving the imaging device within the lumen; and stopping rotation of the imaging device when a signal from the imaging device indicates that the imaging device has reached the ultrasonically recognizable pattern.

27. A method as in claim 26, further comprising deploying a therapeutic element from the catheter while rotating the imaging device.

28. A method as in claim 26, wherein the recognizable pattern comprises a reflective element having a unique shape, and wherein rotation of the imaging device is stopped when a signal from the ultrasonic imaging element indicates detection of the unique shape.

29. A method as in claim 28, wherein the reflective element includes at least one elongate aperture which produces a void in an image generated by the imaging device.

* * * * *